US006338860B1

(12) United States Patent
Taylor

(10) Patent No.: US 6,338,860 B1
(45) **Date of Patent: *Jan. 15, 2002**

(54) COMPOSITIONS FOR PLANTS CONTAINING PHOSPHONATE AND PHOSPHATE SALTS, AND DERIVATIVES THEREOF

(75) Inventor: John B. Taylor, DeLand, FL (US)

(73) Assignee: Foliar Nutrients, Inc., Cairo, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/419,127

(22) Filed: Oct. 15, 1999

Related U.S. Application Data

(63) Continuation-in-part of application No. 09/109,139, filed on Jul. 2, 1998, now Pat. No. 5,997,910, which is a division of application No. 08/812,865, filed on Mar. 6, 1997, now Pat. No. 5,800,837, which is a continuation-in-part of application No. 08/705,594, filed on Aug. 30, 1996, now Pat. No. 5,736,164.

(51) Int. Cl.[7] ........................ A01N 59/26; A01N 57/00; A01N 57/18; A01N 57/10

(52) U.S. Cl. ....................... 424/601; 424/605; 514/129; 514/131; 514/141; 514/142; 514/143

(58) Field of Search ................................ 424/601, 605; 514/129, 131, 141, 142, 143

(56) References Cited

U.S. PATENT DOCUMENTS

| | | | | |
|---|---|---|---|---|
| 1,935,599 | A | 11/1933 | Rippey | 99/1 |
| 3,798,020 | A | 3/1974 | Parham, Jr. et al. | 71/1 |
| 4,075,324 | A | 2/1978 | Thizy et al. | 424/128 |
| 4,119,724 | A | 10/1978 | Thixy et al. | 424/45 |
| 4,139,616 | A | 2/1979 | Ducret et al. | 424/222 |
| 4,542,023 | A | 9/1985 | Lacroix et al. | 514/126 |
| 4,698,334 | A | 10/1987 | Horriere et al. | 514/141 |
| 4,755,614 | A | 7/1988 | Corbet | 558/134 |
| 4,780,458 | A | 10/1988 | Hodakowski et al. | 514/112 |
| 4,806,445 | A | 2/1989 | Horriere et al. | 514/141 |
| 4,849,219 | A | 7/1989 | Staub et al. | 424/605 |
| 4,935,410 | A | 6/1990 | Barlet | 514/75 |
| 5,070,083 | A | 12/1991 | Barlet | 514/144 |
| 5,124,344 | A | 6/1992 | Greiner et al. | 514/383 |
| 5,133,891 | A | 7/1992 | Barr et al. | 252/70 |
| 5,169,646 | A | 12/1992 | Horriere et al. | 424/632 |
| 5,206,228 | A | 4/1993 | Collins | 514/141 |
| 5,246,953 | A | 9/1993 | Greiner et al. | 514/383 |
| 5,290,791 | A | 3/1994 | Greiner et al. | 514/383 |
| 5,342,835 | A | 8/1994 | Pepin et al. | 514/227.5 |
| 5,358,958 | A | 10/1994 | Greiner et al. | 514/383 |
| 5,395,418 | A | 3/1995 | Vetanovetz et al. | 71/29 |
| 5,514,200 | A | 5/1996 | Lovatt | 71/11 |
| 5,585,150 | A | 12/1996 | Sheehan | 428/15 |
| 5,830,255 | A | 11/1998 | Lovatt | 71/11 |

OTHER PUBLICATIONS

*The Use of Red Phosphorus As A Fertilizer*. Pot Trials With Perennial Ryegrass and White Clover; Widdowson, Soil Bureau, and H.P. Rothbaum Chemistry Division, Department of Scientific and Industrial Research, Wellington, pp 427–445 (1964).

*Bacterial Oxidation of Orthophosphite*. George Malancinski and Walter A. Konetzka, Department of Bacteriology, Indian University, Bloomington, Indiana. Feb. 1966 pp. 578–582.

*The Biological Inactivity of Glucose 6–Phosphite, Inorganic Phosphites and Other Phosphites*. H.E. Robertson and P.D. Boyerl, pp 380–395, (Dec. 9, 1995).

*The Merck Index*. An Encyclopedia of Chemicals, Drugs, and Biologicals. Eleventh Edition: 1989, p. 1216.

*Transition of Phosphite to Phosphate in Soils*. Fred Adams and John P. Conrad, pp 361–371 (Jul. 1952).

*Australasian*. Plant Pathology, vol. 19, No. 4, 1990; pp 112–121; 138–139; pp 144–145; pp 921–926.

*The Mode of Action of Phosphite: Evidence for Both Direct and Indirect Modes of Action on Three Phytopthora spp. in Plants*; The American Phytopathological Society; Disease control and Pest Management; vol. 79, No. 9, 1989, pp 921–926, Smillie et al.

*Crystallography and Equilibrium Solubility for Ammonium and Potassium Orthophosphites and Hypophosphites*: A.W. Frazier and K.R. Waerstad, Kluwer Academic Publishers, Fertilizer Research 32, 1992, pp 161–168.

*Effect of Phosphite on Tomato and Pepper Plants and on Susceptibility of Pepper to Phytophthora Root and Crown Rot in Hydroponic Culture*; H. Förster, J.E. Adaskaveg, D.H. Kim, and M.E. Stanghellini, The American Phytopathological Society, Plant Disease, Vo. 82, No. 10, 1998, pp 1165–1169.

Agrichem Manufacturing Industries Pty, Ltd. brochure, Supa Crop, 1990.

*Primary Examiner*—Allen J. Robinson
(74) *Attorney, Agent, or Firm*—Lathrop & Gage L.C.

(57) ABSTRACT

A fungicidal composition for plants containing phosphonate ($PO_3$) and phosphate ($PO_4$) salts, and derivatives thereof is disclosed. The composition provides a single product which may be employed to control a *Phytophthora infestans* infection in plants.

49 Claims, No Drawings

COMPOSITIONS FOR PLANTS CONTAINING PHOSPHONATE AND PHOSPHATE SALTS, AND DERIVATIVES THEREOF

The following application is a continuation-in-part of Ser. No. 09/109,139, filed Jul. 2, 1998, now U.S. Pat. No. 5,997,910 which is a divisional of Ser. No. 08/812,865, filed Mar. 6, 1997, now U.S. Pat. No. 5,800,837, which is a continuation-in-part of Ser. No. 08/705,594, filed Aug. 30, 1996, now U.S. Pat. No. 5,736,164.

FIELD OF INVENTION

The present invention relates to compositions, and methods of use, which provide improved efficacy in controlling Phytophthora infections in plants. More particularly, the composition is comprised of an amount of phosphate ($PO_4$) and phosphonate ($PO_3$), with application of such composition particularly useful in lowering the occurrences of late blight.

BACKGROUND OF INVENTION

From 1845 to 1846, the Irish Potato Famine occurred, which was one of the most devastating crop failures in the history of the world. The potato famine was caused by the disease late blight which resulted in harvested potatoes quickly decaying, making them unsuitable for consumption. The disease is also known to cause defoliation in infected plants. Late blight is caused by a Phytophthora organism infecting a potato or tomato plant. As can be gathered, the Phytophthora organism, if not controlled, can cause major economic damage to agricultural crops, with the resulting damage causing the loss of millions of dollars in crop revenues. Additionally, there is the possibility of significant reduction of the potato and tomato supply available to consumers.

To control late blight, it has been recommended that the contaminated potatoes and/or tomatoes be buried in deep pits and covered by at least two feet of soil. In Northern Latitudes, the potatoes or tomatoes can be spread on the soil surface and allowed to freeze during the winter. These methods temporarily prevent the spread of the disease, but do not prevent infection and attack by the *Phytophthora infestans*. The treatment only addresses plants and crops after they have been destroyed. For this reason, it is desired to have a composition or method that can be administered to potato and tomato fields to actively control and prevent the spread of the *Phytophthora infestans* infestation.

Some species of the Phytophthora genus can be controlled, such as *Phytophthora parasitica*. In particular, fosetyl-al (ethyl phosphonate) can be administered to plants to control diseases such as root rot caused by *Phytophthora parasitica*. As such, it is known that many phosphonate ($PO_3$) compositions are highly effective in combating the disease root rot and, in particular, some of the species of the genus Phytophthora. Unfortunately, fosetyl-al and other phosphonates, alone, do not control late blight and similar Phytophthora diseases caused by the species *Phytophthora sojae*. Thus, it is desired to have a method or composition that readily inhibits infection by and proliferation of *Phytophthora infestans*.

Phosphorus is an essential element in plant nutrition because it governs the energy producing reactions, including those that are oxidative and photo phosphorylative. Phosphorous is essential to the production of adenosine diphosphate (ADP) and adenosine triphosphate (ATP). Energy-rich phosphate bonds of ADP and ATP provide the energy for many of the physiological reactions that occur in plants. As such, various forms of phosphorous are absorbed by plants for use as part of the photosynthetic process.

The element phosphorous appears in numerous general forms, including phosphonate ($PO_3$) and phosphate ($PO_4$). The term "phosphonate," sometimes also referred to as "phosphite," means the salts (organic or inorganic) of either phosphonic acid or phosphorous acid. Phosphonic and phosphorous acids have the formula $H_3PO_3$ and a molecular weight of 82.00. Their structures from the International Union of Pure and Applied Chemistry are shown below:

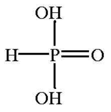

Phosphonic Acid
CA: 13598-36-2

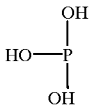

Phosphorous Acid
CA: 10294-56-1

The term "phosphate" means the salts (organic or inorganic) of phosphoric acid having the formula $H_3PO_4$, molecular weight of 98.00 and having the following structure:

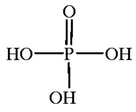

Phosphoric Acid
CA: 7664-38-2

In the past, various phosphonate compounds have been proposed as useful in fungicidal and fertilizer compositions for application to plants. See, e.g. U.S. Pat. Nos. 4,075,324 and 4,119,724 to Thizy, describing phosphorous acid, its inorganic and organic salts, as a plant fungicide; U.S. Pat. No. 4,139,616 to Dueret, describing fungicidal compositions based on phosphorous acid esters and salts thereof; U.S. Pat. No. 4,542,023 to Lacroix et al., describing organophosphorous derivatives as possessing systemic and contact fungistatic and fungicidal activity; U.S. Pat. Nos. 4,698,334, 4,806,445, and 5,169,646 to Horriere et al., describing fungicidal compositions based on alkyl phosphonates; U.S. Pat. Nos. 4,935,410 and 5,070,083 to Barlet, describing fungicidal aluminum tris-alkyl-phosphonate compositions; and U.S. Pat. No. 5,514,200 to Lovatt, describing formulations of phosphorous-containing acid fertilizer for plants. (The teachings of the proceeding U.S. Patents are hereby incorporated by reference.) The above references, disclosing phosphonate compositions, have been found to be effective for protecting plants and, particularly, grape vines, citrus and fruit trees, and tropical plants against fungal attack.

Note that phosphonate ($PO_3$) alone is typically considered an unacceptable source of phosphorus (P) for plants. It is known that $PO_3$ must be converted to $PO_4$ to be utilized by a plant.

Once assimilated, phosphonates ($PO_3$) have been shown to enhance the plant's phytoimmune system. The phosphonate induced stimulation of the phytoimmune system is triggered by the induction of ethylene production, followed by a rapid accumulation of phytoalexins at the site of infection. Phytoalexins are antibiotics which result from the interaction between the host plant and a pathogen. The phytoalexins are synthesized by and accumulate in the plant to inhibit the pathogen. The phytoalexins will accumulate at the site of an infection to prevent further spread of the disease, thereby reducing symptomatic expression of the disease.

In the past, phosphates ($PO_4$) were not viewed as a solution to pathological acerbation of fungal infections or infections produced by other genuses. This is because phosphates ($PO_4$) are viewed primarily as a fertilizer with only limited, or even detrimental, phytoimmune properties. For example, U.S. Pat. No. 5,514,200 teaches that phosphate fertilizers inhibit beneficial symbiosis between plant roots and mycorrhizal fungi, and further promote bacterial and fungical growth in the rhizosphere, including the growth of pathogenic fungi and other small soil-borne organisms. (Col. 2, lines 18–28). Phosphates ($PO_4$) have also been considered to be a competitive inhibitor for phosphonate assimilation, thus inhibiting the ability of phosphonates ($PO_3$) to protect against fungus attack. See, Pegg, K. G. and deBoer, R. F., "Proceedings of the Phosphonic (Phosphorous) Acid Work Shop," *Australiasian Plant Pathology*, Vol. 19 (4), pp. 117 and 144, 1990. Yet further, phosphonates ($PO_3$) and phosphates ($PO_4$) were believed to be "biological strangers," with the presence of phosphonates ($PO_3$) or esters of phosphonates, exerting little or no influence on enzyme reactions involving phosphates. Robertson, H. E. and Boyer, P. D., "The Biological Inactivity of Glucose 6—phosphonate ($PO_3$), Inorganic Phosphites and Other Phosphites," *Archives of Biochemistry and Biophysics*, 62 pp. 380–395 (1956).

Accordingly, the requirements for a successful phosphonate-based fungicide depend on the promotion of the phosphonate-induced pathological acerbation of fungical or other genus infections. More particularly, it is desired to have a composition and/or method that prevents *Phytophthora infestans* infection and destruction of plants.

SUMMARY OF INVENTION

The present invention relates to compositions and methods for use in preventing infection by and manifestations of the genus Phytophthora and, more particularly, *Phytophthora infestans*. The composition will be comprised of phosphate ($PO_4$) and phosphonate ($PO_3$) constituents which, when combined, provide for a synergistic effect that results in the substantial protection against infection of plants by Phytophthora, especially *Phytophthora infestans*. As such, the phosphate and phosphonate constituents can be combined to form a composition, which can be applied to plants, especially tomatoes and potatoes, to prevent infection by *Phytophthora infestans* and diseases caused by such infection. Application can be achieved by using either a dry mix or an aqueous solution.

The preferred composition for preventing Phytophthora will be comprised of potassium phosphonate and potassium phosphate, as it has been found that these two constituents, when combined, will cause a synergistic effect which results in the substantial prevention of infection by Phytophthora. It is believed, that the rate by which infection is prevented is increased by at least 100% when the two constituents are combined, as compared to the additive effect of the combined salts. The two constituents will be combined in an amount sufficient to prevent infection and manifestation by various disease causing organisms, with the particular amounts combined dependent upon the particular species of plant to be treated, the specific disease causing organism to be treated, and the particular phosphate salt and phosphonate salt that will be combined.

The composition should be applied at least once to the plants to be treated. While one application is sufficient, it is typically preferred to make multiple applications. Essentially, any plant infected by Phytophthora can be treated, with it most preferred to apply the composition to potato and tomato plants. It should also be noted that the composition not only inhibits Phytophthora, but is environmentally safe, inexpensive to use, and has low mammalian toxicity.

Preferably, the composition will contain as an active material an effective amount of at least a first salt formula selected from the group consisting of $KH_2PO_3$, and $K_2HPO_3$, and at least a second salt selected from the group consisting of $KH_2PO_4$, $K_2HPO_4$, and $K_3PO_4$, in a mixture with an agriculturally acceptable carrier. The composition preferably comprises an aqueous solution wherein each salt is present in solution from about 20 millimolar to about 5% vol./vol. Alternatively, and more preferably, the actual volume by use will equal 21.7% by weight $PO_4$ and 21.5% by weight $PO_3$. Such composition can then be diluted to between 2% and 4% by volume. Importantly, the $PO_3$ and $PO_4$ must remain soluble, meaning not too much $PO_3$ and $PO_4$ can be added, otherwise the $PO_3$ and $PO_4$ will precipitate.

Phosphonate salts useful in the practice of the invention also include those organic and inorganic salts taught by U.S. Pat. Nos. 4,075,324 and 4,119,724 to Thizy et al., (see, e.g., col. 1, In. 51–69 through col. 2, In. 1–4).

DETAILED DESCRIPTION OF THE PREFERRED EMBODIMENT

The present invention relates to compositions and methods for use in preventing diseases, such as late blight, caused by the genus Phytophthora. In particular, the present invention relates to compositions and methods for use in preventing plant diseases caused by *Phytophthora infestans*. The composition is comprised of a phosphate ($PO_4$) constituent and phosphonate ($PO_3$) constituent, with it most preferred that a composition comprised of potassium phosphonate and potassium phosphate be used. Once the composition is formed, it can be applied to plants to prevent infection by *Phytophthora infestans* and manifestations related to the infection. The composition can be applied as either a dry mix or an aqueous solution to plants prior to infection by the *Phytophthora infestans* organism.

The composition for preventing *Phytophthora infestans* is prepared by combining phosphonate and phosphate constituents. Any of a variety of phosphates are suitable for use, including $K_2HPO_4$, $K_3PO_4$, $KH_2PO_4$, $(NH_3)_2$ $HPO_4$, $(NH_3)$ $H_2PO_4$, and combinations thereof. The phosphonates, like the phosphates, can be selected from any of a variety of compositions, including $K_2HPO_3$, $KH_2PO_3$, $(NH_3)_2$ $HPO_3$, $(NH_3)$ $H_2PO_3$, and combinations thereof. Any phosphate and phosphonate constituent combination can be used as long as infection by and manifestation of Phytophthora infestations is inhibited. Additionally, it is necessary for the constituents to have suitable solubility in a carrier and to be of a constitution to allow easy distribution in an area where plants to be treated are grown. More preferably, the phosphonate and phosphate constituents, when combined, will have a synergistic effect in inhibiting *Phytophthora infestans*. The most preferred phosphate $PO_4$) and phosphonate $PO_3$) constituents for use in preventing *Phytophthora infestans* infection are combinations of $K_2HPO_3$ and $K_2HPO_4$. As such, the phosphate ($PO_4$) and phosphonate ($PO_3$) constituents are combined to form the composition used to prevent *Phytophthora infestans* infection.

While the discussed constituents are preferred for use in treating plants and preventing infection by the Phytophthora organism, variations of the phosphate and phosphonate constituents can be used. As such, it is preferred if the compound comprises a fungicidally effective amount of at least a first salt having the following formula:

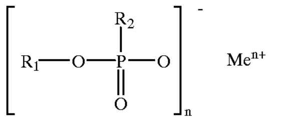

and a second salt having the following formula:

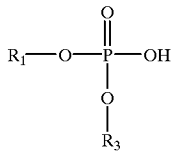

where $R_1$ is selected from the group consisting of H, K, an alkyl radical containing form 1 to 4 carbon atoms, halogen-substituted alkyl or nitro-substituted alkyl radical, an alkenyl, halogen-substituted alkenyl, alkynl, halogen-substituted alkynl, alkoxy-substituted alkyl radical, ammonium substituted by alkyl and hydroxy alkyl radicals;

$R_2$ and $R_3$ are selected from a group consisting of H and K;

Me is selected from a group consisting of K, alkaline earth metal cations, aluminum atom, and the ammonium cation; and n is a whole number from 1 to 3, equal to the valence of Me.

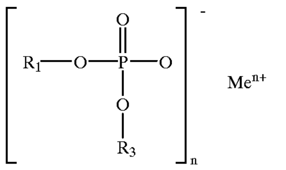

The constituents should be preferably mixed with a suitable carrier to facilitate distribution to an area where the plants to be treated are grown. The carrier should be agriculturally acceptable, with water ($H_2O$) most preferred.

As an example of how to form the composition, it is preferred to first form a potassium phosphonate aqueous solution, with the phosphonate formation as follows:

$H_3PO_3$ is produced by the hydrolysis of phosphorus trichloride according to the reaction: $PCl_3+3H_2O>H_3PO_3+3HCl$. The HCl is removed by stripping under reduced pressure, and the phosphonic acid ($H_3PO_3$) is sold as a 70% acid solution.

The phosphonic acid is then neutralized in aqueous solution by potassium hydroxide according to the reaction: $H_3PO_3+KOH>KH_2PO_3+H_2O$ to about pH 6.5, and to produce a 0-22-20 liquid weighing 11.15 lbs./gal. This solution is commercially available and is sold under the trademark “Phos-Might” by Foliar Nutrients, Inc., Cairo, Ga. 31728.

The phosphate ($P_4$) is produced by reacting mono potassium phosphate (0-51.5-34) with 45% potassium hydroxide in aqueous solution to produce dipotassium phosphate, by the following reaction: $KH_2PO_4+KOH>K_2HPO_4+H_2O$ with a product density of 1.394 at 20° C. and a solution pH of 7.6 producing a 0-18-20 analysis. This solution is commercially available and is sold under trademark “K-Phos” by Foliar Nutrients, Inc., Cairo, Ga. 31724.

After the potassium phosphonate and potassium phosphate constituents, or other phosphonate and phosphate constituents, are formed, they can be combined to produce the potassium phosphonate and potassium phosphate composition. This composition is used to then treat plants for the prevention of infection by the Phytophthora genus, especially *Phytophthora infestans.*

Varying amounts of each compound, for example, $K_2HPO_3$, $KH_2PO_3$, $K_2HPO_4$, or $KH_2PO_4$ in an aqueous solution, are combined at rates ranging from 20 millimolar to 5% vol./vol., depending on crop host and the pathogen complex and level of infection. Alternatively, the amount of the first salt is equal to one part by weight and the amount of the second salt is equal to between 0.001 and 1,000 parts by weight. It is preferred if the composition is comprised of 21.7% $K_2HPO_4$ and 21.5% $K_2HPO_3$ or 11.8% $PO_4^{-3}$ and 10.7% $PO3^{-2}$, all of which are soluble.

Once formed, the composition will be applied to various plants to prevent *Phytophthora infestans* infection. The preferable method of application is foliar, either by ground or aerial equipment, but is not limited to that method alone. Injection or soil applications, for example, could also be efficacious depending on specific crops and pathogens. While it is preferred to apply the composition in an aqueous solution, other forms of application may be used, including dusts, flowables, water dispersable granules, granules and inert emulsions, as well as oils. At least one application should be made; however, multiple applications of the composition can be made.

The inventive composition has utility on fruit crops, agronomic crops, ornamentals, trees, grasses, vegetables, grains, and floricultural crops, as well as some aquatic crops, including water cress. The crops most likely infected by *Phytophthora infestans* are potatoes (*Solanum tuberosum*) and tomatoes (*Lycopersicon esculentum*). As such, the present composition is especially useful in treating potato and tomato plants to prevent Phytophthora infection.

The following examples set forth the preferred concentrations and techniques for formulation thereof, as well as methods of application, use and test results demonstrating the efficacy of the inventive concentration in protecting plants against attack by *Phytophthora infestans.* It is to be understood, however, that these Examples are presented by way of illustration only, and nothing therein shall be taken as a limitation upon the overall scope of the invention. The specific components tested in the Examples were prepared and applied as follows.

In each of Examples 1 and 2, treatments were applied as a one gallon solution by a back pack sprayer, maintained at about 60 psi, in sufficient quantities of water to achieve thorough coverage. All treatments were applied to the appropriate number of experimental units assigned in a randomized complete block (CRB) design replicated four times.

As used in the examples, “Percent Late Blight” means the percent of plants that exhibit blight. “Lesions Per Plant” relate to the number of lesions on a particular plant caused by the infectious inoculum. The “No. Infected Leaflets” relates to the number of infected leaves per plant.

EXAMPLES

Example 1

Potatoes (*Solanum tuberosum*, variation Atlantic) were infected with a pathogen, *Phytophthora infestans*, to determine whether suitable treatments could be developed to eliminate the pathogen from the infected plants and, more importantly, prevent infection of the plants by the pathogen. The Phytophthora pathogen causes late blight in infected plants. The plants were treated with the below listed compositions, twice, with the applications being seven (7) days apart. The composition of the inoculant added to the plants is listed below in the table. One week (7 days) after the last inoculation was made to the plants, the potato plants were then infected with the pathogen, *Phytophthora infestans*. The infectious inoculum was equal to 12,000 sporangia per millimeter (ml), with 20 ml administered per plant. The Genotype of the pathogen was US-8 and the Matingtype was A2. Seven days after inoculation with the pathogen, the results were tabulated to determine the percentage of blight in the plants and the number of lesions per plant. Additionally, the number of infected leaflets per plant were tabulated. The results are as follows:

Summary Late Blight Observations FNX Greenhouse Experiment

| TREATMENT | RATE/A | % LATE BLIGHT | LESIONS PER PLANT | NO. INFECTED LEAFLETS PER PLANT |
|---|---|---|---|---|
| $K_2HPO_3$ + $K_2HPO_4$ | 1% + 1% | 0.39 | 0.5 | 0.5 |
| Cu-EDDHA | 0.2 lb. ai | 12.30 | 35.3 | 26.9 |
| $K_2HPO_3$ | 1% | 1.85 | 2.4 | 1.8 |
| $K_2HPO_4$ | 1% | 18.45 | 41.4 | 31.1 |
| CONTROL | | 28.12 | 84.4 | 50.1 |

Tests were made on single 6" pots×4 reps in CRB design.

As can be seen, an inoculum of just phosphonate ($PO_3$) showed good results in controlling the blight. However, better results were achieved using the phosphate ($PO_4$) and phosphonate ($PO_3$) composition. The ($PO_4$) and ($PO_3$) combination demonstrated exceptional blight depression, indicating that potato blight can be better controlled using a composition comprised of ($PO_3$) and ($PO_4$). This indicates that a synergistic effect is achieved with a ($PO_3$) and ($PO_4$) combination.

Example 2

Tomatoes (*Lycopersicon esculentum*, FL 40) were infected with a pathogen, *Phytophthora infestans*, to determine whether suitable treatments could be developed to prevent infection of the plants by the pathogen. The Phytophthora pathogen causes late blight in infected plants. The plants were treated with the below listed compositions, twice, with the application dates being seven (7) days apart. The composition of the inoculant added to the plants is listed below in the table. One week (7 days) after last inoculation was made to the plants, the tomato plants were then infected with the pathogen, *Phytophthora infestans*. The infectious inoculum was equal to 12,000 sporangia per millimeter (ml), with 20 ml administered per plant. The Genotype of the pathogen was US-17 and the Matingtype was Al. Seven days after inoculation with the pathogen, the results were tabulated to determine the percentage of blight in the plants and the number of lesions per plant. Additionally, the number of infected leaflets per plant were tabulated. The results are as follows:

Greenhouse Tomato Late Blight Trial

| TREATMENT | RATE/A | LESIONS/PLANT | NO. INFECTED LEAFLETS/PLANT |
|---|---|---|---|
| $K_2HPO_3$ + $K_2HPO_4$ | 2% | 6.0 | 2.5 |
| SIMAZINE 4L | 0.1 lb. ai | 52.3 | 36.8 |
| $K_2HPO_3$ | 1% | 56.7 | 21.5 |
| $K_2HPO_4$ | 1% | 74.8 | 36.5 |
| CONTROL | | 66.8 | 33.8 |

Excellent results were achieved using the phosphate ($PO_4$) and phosphonate ($PO_3$) composition. The ($PO_4$) and ($PO_3$) combination demonstrated exceptional blight depression, indicating that the blight can be better controlled using a composition comprised of ($PO_3$) and ($PO_4$). This indicates that a synergistic effect is achieved with a ($PO_3$) and ($PO_4$) combination.

The above Examples demonstrate that the inventive compositions are useful in protecting plants against attack by the *Phytophthora infestans* infection with the application of one solution.

The disclosures in all references cited herein are incorporated by reference.

Alternatively, the composition can be used to prevent infection by Phycomycetes, Ascomycetes, and other fungal pathogens, as well as bacteria.

Thus, there has been shown and described a method relating to the use of a phosphonate ($PO_3$) and phosphate ($PO_4$) composition which provides improved efficacy in controlling Phytophthora infections in plants which fulfills all the objects and advantages sought therefore. It is apparent to those skilled in the art, however, that many changes, variations, modifications, and other uses and applications for a phosphonate ($PO_3$) and phosphate ($PO_4$) composition are possible, and also such changes, variations, modifications, and other uses and applications of a phosphonate ($PO_3$) and phosphate ($PO_4$) composition which do not depart from the spirit and scope of the invention are deemed to be covered by the invention, which is limited only by the claims which follow.

What is claimed is:

1. A composition for preventing and controlling diseases in plants caused by Phytophthora, whereby said composition comprises an effective amount of at least a first salt having the following formula:

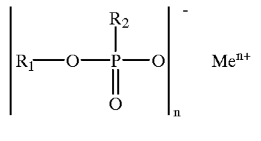

and a second salt having the following formula:

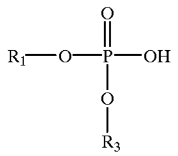

where $R_1$ is selected from the group consisting of H, K, an alkyl radical containing from 1 to 4 carbon atoms, halogen-substituted alkyl or nitro-substituted alkyl radical, an alkenyl, halogen-substituted alkenyl, alkynyl, halogen-substituted alkynyl, alkoxy-substituted alkyl radical, ammonium substituted by alkyl or hydroxy alkyl radicals;

$R_2$ and $R_3$ are selected from the group consisting of H and K;

Me is selected from the group consisting of K, alkaline earth metal cations, an aluminum atom, and an ammonium cation; and, n is a whole number equal to between 1 and 3, equal to the valence of Me;

whereby said effective amounts of said first salt and said second salt, when combined, have a synergistic effect on said disease prevention and control.

2. The composition of claim 1 wherein said first salt is selected from the group consisting of $K_2HPO_3$, $KH_2PO_3$, $(NH_3)H_2PO_3$, and $(NH_3)_2HP_3$; and said salt is selected from the group consisting of $K_2HPO_4$, $KH_2PO_4$, and $K_3PO_4$.

3. The composition of claim 1 wherein said composition is in an aqueous solution, wherein each said first and second salt is present in solution from about 20 millimolar to about 5% vol./vol.

4. The composition of claim 1 wherein said first salt is equal to one part by weight and said second salt is equal to between 0.001 and 1,000 parts by weight.

5. The composition of claim 1 wherein said composition prevents and controls diseases caused by *Phytophthora infestans* and *Phytophthora sojae* species.

6. The composition of claim 1 wherein the plants are tomato and potato species.

7. The composition of claim 5 wherein said composition prevents and controls diseases caused by *Phytophthora infestans.*

8. The composition of claim 1 wherein Me is potassium.

9. The composition of claim 2 wherein said first salt is selected from the group consisting of $K_2HPO_3$ and $KH_2PO_3$.

10. A composition for preventing and controlling diseased in plants caused by Phytophthora, whereby said composition comprises an effective amount of at least a first salt having the following formula:

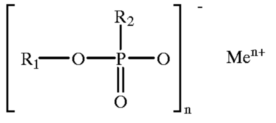

and a second salt having the following formula:

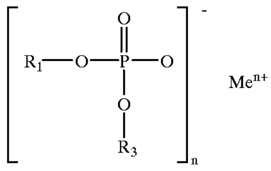

where $R_1$ is selected from the group consisting of H, K, an alkyl radical containing from 1 to 4 carbon atoms, halogen-substituted alkyl or nitro-substituted alkyl radical, an alkenyl, halogen-substituted alkenyl, alkynyl, halogen-substituted alkynyl, alkoxy-substituted alkyl radical, ammonium substituted by alkyl or hydroxy alkyl radicals;

$R_2$ and $R_3$ are selected from a group consisting of H and K;

Me is selected from a group consisting of K, alkaline earth metal cations, or aluminum atom; ammonium cation; and n is a whole number from 1 to 3, equal to the valence of Me;

whereby said effective amounts of said first salt and said second salt, when combined, have a synergistic effect on said disease prevention and control.

11. The composition of claim 10 wherein said composition comprises an aqueous solution, wherein each said first and second salt being present in solution from about 20 millimolar to about 5% vol./vol.

12. The composition of claim 10 wherein said first salt is selected from the group consisting of $K_2HPO_3$, $KH_2PO_3$, $(NH_3)_2HPO_3$; and $(NH_3)H_2PO_3$; and second salt is selected from the group consisting of $K_2HPO_4$, $KH_2PO_4$, $K_3PO_4$ $(NH_3)_2HPO_3$, and $(NH_3)H_2PO_3$.

13. The composition of claim 10 wherein the amount of said first salt is one part by weight and the amount of said second salt is between 0.001 and 1,000 parts by weight.

14. A composition for preventing diseases in plants caused by Phytophthora, and other fungal and bacterial diseases whereby said composition comprises an effective amount of at least a first salt having the following formula:

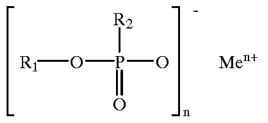

and a second salt having the following formula:

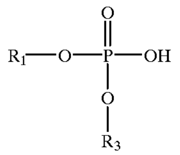

where $R_1$ is selected from the group consisting of H, K, an alkyl radical containing from 1 to 4 carbon atoms, halogen-substituted alkyl or nitro-substituted alkyl radical, an alkenyl, halogen-substituted alkenyl, alkynyl, halogen-substituted alkynyl, alkoxy-substituted alkyl radical, ammonium substituted by alkyl or hydroxy alkyl radicals;

$R_2$ and $R_3$ are selected from the group consisting of H and K;

Me is selected from the group consisting of k, alkaline earth metal cations, an aluminum atom, and an ammonium cation; and, n is a whole number equal to between 1 and 3, equal to the valence of Me, whereby said first salt and said second salt, when combined, have a synergistic effect so that disease control is at least 100% greater than the additive affect of the combined salts.

15. The composition of claim 10 wherein said composition prevents and controls diseases caused by *Phytophthora infestans* and *Phytophthora sojae* species.

16. The composition of claim 15 wherein said composition prevents and controls diseases caused by *Phytophthora infestans.*

17. The composition of claim 10 wherein the plants are tomato and potato species.

18. The composition of claim 10 wherein Me is potassium.

19. The composition of claim 12 wherein said first salt is selected from the group consisting of $K_2HPO_3$ and $KH_2PO_3$.

20. A method for preventing and controlling diseases caused by Phytophthora in plants, comprising:

(a) forming a composition comprising an effective amount of a first salt of the formula:

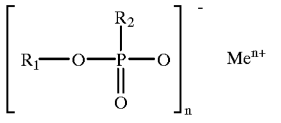

and a second salt having the following formula:

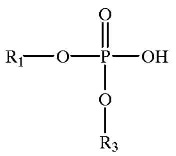

where $R_1$ is selected from the group consisting of H, K, an alkyl radical containing from 1 to 4 carbon atoms, halogen-substituted alkyl or nitro-substituted alkyl radical, an alkenyl, halogen-substituted alkenyl, alkynyl, halogen-substituted alkynyl, alkoxy-substituted alkyl radical, ammonium substituted by alkyl or hydroxy alkyl radicals;

$R_2$ and $R_3$ are selected from the group consisting of H and K;

Me is selected from the group consisting of K, alkaline earth metal cations, an aluminum atom, and an ammonium cation; and, n is a whole number equal to between 1 and 3, equal to the valence of Me; and, (b) applying a synergistic fungicidally effective amount of said composition at least once to the plant.

21. The method of claim 20 wherein said first salt is selected from the group consisting of $K_2HPO_3$, $KH_2PO_3$, $(NH_3)H_2PO_3$, and $(NH_3)_2HPO_3$; and said second salt is selected from the group consisting of $K_2HPO_4$, $KH_2PO_4$, and $K_3PO_4$.

22. The method of claim 20 wherein said first salt is $K_2HPO_3$ and said second salt is $K_2HPO_4$.

23. The method of claim 20 wherein said composition comprises an aqueous solution, wherein each said first and second salt being present in solution from about 20 millimolar to about 5% vol./vol.

24. The method of claim 20 wherein said first salt is equal to one part by weight and said second salt is equal to between 0.001 and 1,000 parts by weight.

25. The method of claim 20 wherein said composition can be applied to the plant prior to or after infection by the Phytophthora organism.

26. The method of claim 20 wherein said composition is used to prevent and control infection by *Phytophthora infestans* or *Phytophthora sojae.*

27. The method of claim 26 wherein said composition prevents and controls diseases caused by *Phytophthora infestans.*

28. The method of claim 20 wherein Me is potassium.

29. The method of claim 21 wherein said first salt is selected from the group consisting of $K_2HPO_3$ and $KH_2PO_3$.

30. A method for preventing and controlling diseases caused by Phytophthora in plants comprising applying to the plants in synergistic fungicidally effective amounts a composition comprising:

(a) an aqueous solution of $H_3PO_3$ and KOH, and (b) an aqueous solution of monopotassium phosphate and KOH.

31. The method of claim 30 wherein the amount of potassium phosphonate in said aqueous solution (a) and the amount of potassium phosphate in said aqueous solution (b) is each present in said composition in an amount from about 20 millimolar to about 5% vol./vol.

32. The method of claim 30 wherein the amount of potassium phosphonate prepared from solution (a) in said composition is one part by weight and the amount of potassium phosphate prepared from solution (b) in said composition is between 0.001 and 1,000 parts by weight.

33. The method of claim 30 wherein said composition is used to prevent and control infection by *Phytophthora infestans* or *Phytophthora sojae.*

34. The method of claim 33 wherein said composition is used to prevent and control infection by *Phytophthora infestans.*

35. A method for preventing and controlling diseases caused by Phytophthora in plants comprising applying to the plants in synergistic fungicidally effective amounts a composition prepared by mixing:

(a) an aqueous solution of $H_3PO_3$ and KOH, and (b) an aqueous solution of monopotassium phosphate and KOH.

36. The method of claim 35 wherein the amount of potassium phosphonate in said aqueous solution (a) and the amount of potassium phosphate in said aqueous solution (b) is each present in said composition in an amount from about 20 millimolar to about 5% vol./vol.

37. The method of claim 35 wherein the amount of potassium phosphonate prepared from solution (a) in said composition is one part by weight and the amount of potassium phosphate prepared from solution (b) in said composition is between 0.001 and 1,000 parts by weight.

38. The method of claim 35 wherein said composition is used to prevent and control infection by *Phytophthora infestans* or *Phytophthora sojae.*

39. The method of claim 38 wherein said composition is used to prevent and control infection by *Phytophthora infestans.*

40. A method for preventing and controlling diseases caused by Phytophthora in plants comprising applying to the plants in synergistic fungicidally effective amounts a composition comprising:

(a) an aqueous solution of $H_3PO_3$ and KOH, and (b) an aqueous solution of dipotassium phosphate.

41. The method of claim 40 wherein the amount of potassium phosphonate in said aqueous solution (a) and the amount of dipotassium phosphate in said aqueous solution (b) is each present in said composition in an amount from about 20 millimolar to about 5% vol./vol.

42. The method of claim 40 wherein the amount of potassium phosphonate prepared from solution (a) in said composition is one part by weight and the amount of dipotassium phosphate prepared from solution (b) in said composition is between 0.001 and 1,000 parts by weight.

43. The method of claim 40 wherein said composition is used to prevent and control infection by *Phytophthora infestans* or *Phytophthora sojae.*

44. The method of claim 43 wherein said composition is used to prevent and control infection by *Phytophthora infestans.*

45. A method for preventing and controlling fungus diseases caused by Phytophthora in plants comprising applying to the plants in synergistic fungicidally effective amounts a composition prepared by mixing:

(a) an aqueous solution of $H_3PO_3$ and KOH, and (b) an aqueous solution of dipotassium phosphate.

46. The method of claim 45 wherein the amount of potassium phosphonate in said aqueous solution (a) and the amount of dipotassium phosphate in said aqueous solution (b) is each present in said composition in an amount from about 20 millimolar to about 5% vol./vol.

47. The method of claim 45 wherein the amount of potassium phosphonate prepared from solution (a) in said composition is one part by weight and the amount of dipotassium phosphate prepared from solution (b) in said composition is between 0.001 and 1,000 parts by weight.

48. The method of claim 45 wherein said composition is used to prevent and control infection by *Phytophthora infestans* or *Phytophthora sojae.*

49. The method of claim 48 wherein said composition is used to prevent and control infection by *Phytophthora infestans.*

* * * * *